United States Patent
Zunker et al.

(10) Patent No.: US 6,695,763 B2
(45) Date of Patent: Feb. 24, 2004

(54) INCONTINENCE INSERT DEVICE AND METHOD OF USING SAME

(75) Inventors: MaryAnn Zunker, Oshkosh, WI (US); Herb F. Velazquez, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 10/039,230

(22) Filed: Jan. 2, 2002

(65) Prior Publication Data

US 2003/0125603 A1 Jul. 3, 2003

(51) Int. Cl.[7] ............................ A61F 2/00; A61F 13/20
(52) U.S. Cl. ..................................... 600/29; 604/13
(58) Field of Search .................. 600/29, 30; 604/15, 604/286, 359, 369, 904, 14, 385.18, 517, 279, 13, 18; 601/70, 72

(56) References Cited

U.S. PATENT DOCUMENTS

| | | |
|---|---|---|
| 2,057,206 A | 10/1936 | Pohl |
| 2,298,752 A | 10/1942 | Crockford |
| 2,355,628 A | 8/1944 | Calhoun |
| 2,401,585 A | 6/1946 | Seidler |
| 2,491,017 A | 12/1949 | Robinson |
| 2,519,912 A | 8/1950 | Laun |
| 2,739,593 A | 3/1956 | McLaughlin |
| 2,938,519 A | 5/1960 | Marco |
| 3,032,036 A | 5/1962 | Rader et al. |
| 3,034,508 A | 5/1962 | Nalle, Jr. |
| 3,090,385 A | 5/1963 | Brecht |
| 3,409,011 A | 11/1968 | Mittag |
| 3,543,754 A | 12/1970 | Jones, Sr. |
| 3,643,661 A | 2/1972 | Crockford |
| 3,646,929 A | 3/1972 | Bonnar |
| 3,765,417 A | 10/1973 | Crockford |
| 3,799,165 A | 3/1974 | Wennerblom et al. |
| 3,885,563 A | 5/1975 | Johnson et al. |
| 3,918,452 A | 11/1975 | Cornfeld |

FOREIGN PATENT DOCUMENTS

| | | | |
|---|---|---|---|
| DE | 1815375 | * | 9/1970 |
| EP | 0610951 A1 | | 8/1974 |
| EP | 0 460 807 A2 | * | 12/1991 |
| EP | 0 264 258 B1 | * | 4/1992 |
| EP | 0 498 912 A1 | * | 8/1992 |
| EP | 0 363 421 B2 | * | 10/1995 |
| EP | 0 714 271 B1 | * | 5/1998 |
| GB | 1116742 | * | 6/1968 |
| WO | WO 88/10106 | * | 12/1988 |

OTHER PUBLICATIONS

U.S. application Ser. No. 09/675,458, Incontinence Insert Applicators And Methods For Their Use, Filed Sep. 28, 2000.*
U.S. application Ser. No. 09/675,459, "Urinary Incontinence Device And Method Of Making Same,"Filed Sep. 28, 2000.*
U.S. application Ser. No. 09/675,460, Resilient Incontinence Insert And A Method Of Making The Same, Filed Sep. 28, 2000.*
U.S. application Ser. No. 10/038,765, "Tampon Applicator Assembly And Method Of Using Same,"Filed Jan. 2, 2002.*

Primary Examiner—Eric F. Winakur
Assistant Examiner—Nikita R Veniaminov
(74) Attorney, Agent, or Firm—Brinks Hofer Gilson & Lione (57) ABSTRACT

An incontinence insert device and a method for placing an incontinence insert within a vagina. The device includes an expandable insert and a single piece applicator. The applicator assists in the proper placement of the insert into the vagina. Once inside the vagina, the insert expands to its expanded position, providing support to the urinary tract and thereby decreasing the tendency for the involuntary escape of urine.

22 Claims, 6 Drawing Sheets

U.S. PATENT DOCUMENTS

| | | | |
|---|---|---|---|
| 3,971,378 A | | 7/1976 | Krantz |
| 3,983,875 A | | 10/1976 | Truman |
| 4,019,498 A | | 4/1977 | Hawtrey et al. |
| 4,077,409 A | * | 3/1978 | Murray et al. ............... 604/15 |
| 4,139,006 A | | 2/1979 | Corey |
| 4,148,317 A | | 4/1979 | Loyer |
| 4,212,301 A | | 7/1980 | Johnson |
| 4,398,532 A | | 8/1983 | Sweeney, III |
| 4,498,899 A | | 2/1985 | Gross |
| 4,536,178 A | | 8/1985 | Lichstein et al. |
| 4,573,963 A | | 3/1986 | Sheldon |
| 4,573,964 A | | 3/1986 | Huffman |
| 4,857,044 A | | 8/1989 | Lennon |
| 4,920,986 A | | 5/1990 | Biswas |
| 4,921,474 A | | 5/1990 | Suzuki et al. |
| 4,960,417 A | * | 10/1990 | Tarr et al. ................... 604/15 |
| 4,973,302 A | | 11/1990 | Armour et al. |
| 5,007,894 A | | 4/1991 | Enhorning |
| 5,036,867 A | | 8/1991 | Biswas |
| 5,045,079 A | | 9/1991 | West |
| 5,080,659 A | | 1/1992 | Nakanishi |
| 5,135,475 A | * | 8/1992 | Nakanishi et al. ........... 604/14 |
| 5,386,836 A | | 2/1995 | Biswas |
| 5,395,308 A | | 3/1995 | Fox et al. |
| 5,395,309 A | | 3/1995 | Tanaka et al. |
| 5,445,605 A | | 8/1995 | Plüss |
| 5,554,109 A | | 9/1996 | Frayman |
| 5,609,559 A | | 3/1997 | Weitzner |
| 5,609,586 A | | 3/1997 | Zadini et al. |
| 5,618,256 A | | 4/1997 | Reimer et al. |
| 5,659,934 A | | 8/1997 | Jessup et al. |
| 5,755,906 A | | 5/1998 | Achter et al. |
| 5,782,779 A | * | 7/1998 | Kilgore ....................... 601/70 |
| 5,785,640 A | | 7/1998 | Kresch et al. |
| 5,795,346 A | | 8/1998 | Achter et al. |
| 5,816,248 A | | 10/1998 | Anderson et al. |
| 5,873,971 A | | 2/1999 | Balzar |
| 5,988,386 A | | 11/1999 | Morrow |
| 6,019,743 A | | 2/2000 | Cole et al. |
| 6,039,716 A | | 3/2000 | Jessup et al. |
| 6,039,828 A | | 3/2000 | Achter et al. |
| 6,056,714 A | | 5/2000 | McNelis et al. |
| 6,071,259 A | | 6/2000 | Steiger et al. |
| 6,090,038 A | | 7/2000 | Zunker et al. |
| 6,090,098 A | | 7/2000 | Zunker et al. |
| 6,095,998 A | | 8/2000 | Osborn, III et al. |
| 6,142,928 A | | 11/2000 | Zunker et al. |
| 6,248,089 B1 | | 6/2001 | Porat |
| 6,270,470 B1 | | 8/2001 | Buck et al. |
| 6,358,223 B1 | * | 3/2002 | Mackay et al. ............... 604/15 |

* cited by examiner

INCONTINENCE INSERT DEVICE AND METHOD OF USING SAME

FIELD OF THE INVENTION

The present invention relates to a urinary incontinence device and a method of using the device. More specifically, this invention relates to a urinary incontinence device which is designed to be placed inside a vagina for providing support to the urethra to prevent the involuntary urine loss commonly associated with stress urinary incontinence.

BACKGROUND

Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder and cause the involuntary release of urine. The frequency and severity of such urine loss can increase as the muscles and tissues near the urethro-vaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle cannot close properly, therefore, the tendency for involuntary urine loss increases. As the world's female population ages, there is an ever increasing need for a nonsurgical procedure to reduce the involuntary urine loss commonly associated with stress urinary incontinence. Today, there are a number of products available for this purpose. Essentially all of these products can only be purchased with a prescription and they need to be physically inserted and/or adjusted by a medical doctor or a nurse practitioner in order to perform correctly.

In view of the general lack of commercially available non-prescription urinary incontinence devices, it is recognized that there is a need for an effective urinary incontinence device which can be purchased without a prescription. There is also a need for a urinary incontinence device which is more user friendly and can be managed by the consumer without the intervention of a medical practitioner. Furthermore, there is a need for a urinary incontinence device which is easy for women to insert into and remove from their bodies, is more comfortable to wear, and which provides psychological and realistic assurance that it is capable of properly performing over an extended period of time.

BRIEF SUMMARY

In one aspect of the invention, a device is provided for reducing the occurrence and/or severity of female incontinence. The device includes an incontinence insert, a withdrawal member, and a single piece applicator. The incontinence insert is adapted to be placed in a vagina to at least partially reduce incontinence. The insert has a first end portion and a second end portion. The withdrawal member is attached to at least one of the first end portion and the second end portion of the incontinence insert, and the withdrawal member includes a stopping member. The single piece applicator has a leading end portion and a trailing end portion, and the leading end portion engages the incontinence insert. The trailing end portion is adapted to releasably secure the stopping member against movement in at least one direction.

In another aspect of the invention, a device includes a single piece applicator having a trailing end portion and a leading end portion, and an expandable insert having an expanded position and a contracted position. The insert is adapted to be placed in a vagina to at least partially reduce incontinence. The leading end portion of the applicator engages the insert while the insert is in its contracted position.

In yet another aspect of the invention, a method of placing an incontinence insert within a vagina is provided. The method includes inserting an incontinence device into a vagina, the device including a single piece applicator and an expandable incontinence insert. The insert is released from the single piece applicator. The single piece applicator is then withdrawn from the vagina.

Other aspects of the invention will be apparent to those skilled in the art in view of the claims following the detailed description of the presently preferred embodiments.

DETAILED DESCRIPTION

The present invention provides an easy to use, comfortable, and effective device and method for reducing or eliminating female urinary incontinence. The devices according to the present invention all include an incontinence insert and a single piece applicator. The single piece applicator cooperates with the insert during insertion of the device into the vagina. The insert is the leading edge of the device, and thus provides a softer, more comfortable insertion than would a leading end of some other applicators. After the insert is properly positioned within the body, the insert and the single piece applicator are separated, and the applicator is withdrawn while the insert is left in the body. The single piece applicator does not include a plunger, and thus may be more economical to make and may be made of smaller dimensions.

Figure 1A:
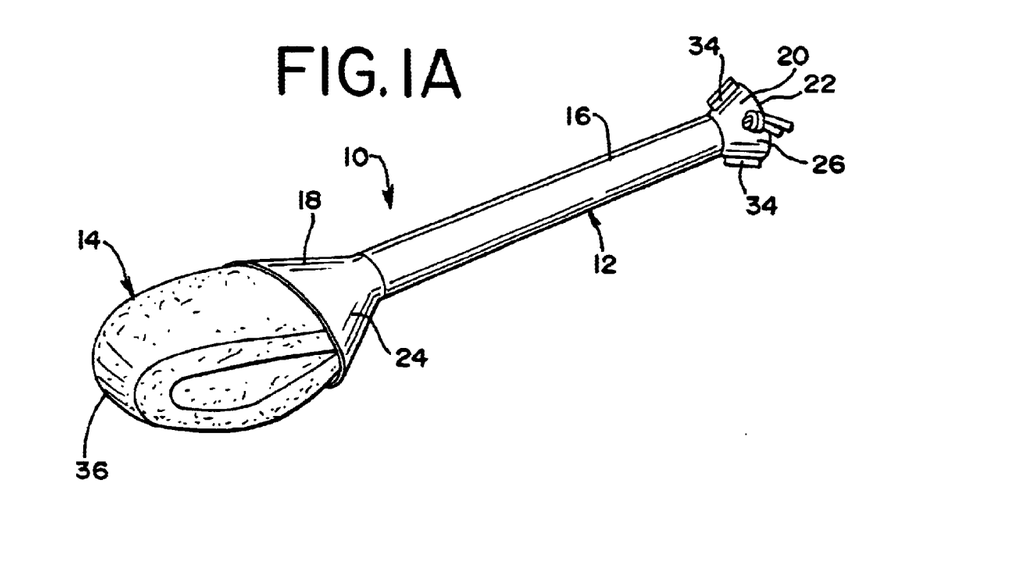
FIG. 1A is a perspective view of one embodiment of a urinary incontinence device according to the present invention.
Figure 1B:
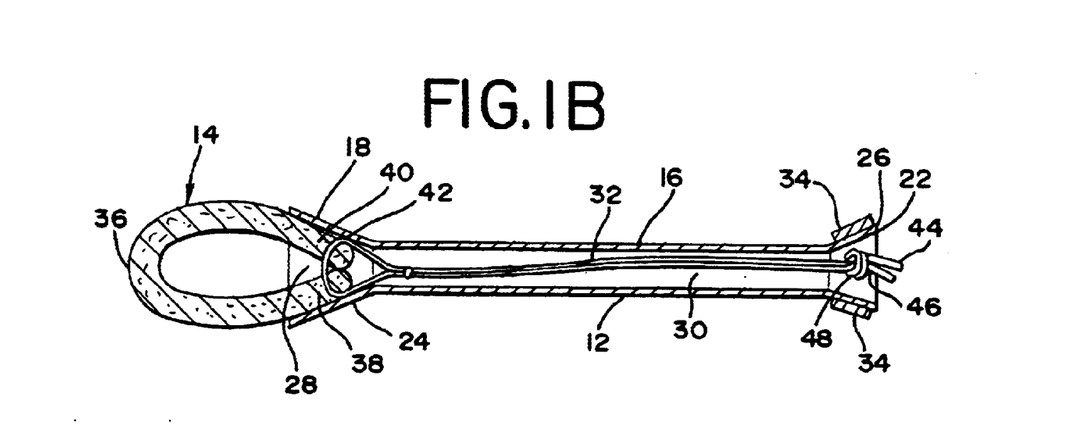
FIG. 1B is a cross-sectional view of the device of FIG. 1A.

Referring now to FIGS. 1A and 1B, one embodiment of an incontinence insert device in accordance with the present invention is shown generally at 10. The device 10 includes a single piece applicator 12 and an incontinence insert 14. The applicator 12 includes an elongated portion 16, a leading end portion 18, and a trailing end portion 20, which has a trailing edge 22. In the embodiment shown in FIGS. 1A and 1B, the leading end portion 18 and the trailing end portion 20 have generally conical shapes 24, 26, respectively. The conical shape 24 of the leading end portion 18 defines a cavity 28. The applicator 12 has a hollow interior or passageway 30 which allows a withdrawal member 32 to extend therethrough from the leading end portion 18 to the trailing end portion 20. The withdrawal member 32 allows the user to withdraw the insert 14 at a time after it has been inserted into the body. The trailing end portion 20 preferably includes at least one orientation indicator 34, such as one or more tabs, which assist the user in properly orientating the applicator, and thus the insert, within the vagina, as described in more detail below.

The applicators of the present invention should be made of a biocompatible material, such as a paperboard stock, or a plastic. The applicators preferably are about 85 mm to about 140 mm in length, more preferably about 110 to about 115 mm. In a preferred embodiment, the applicators have an elliptical cross-section, which maximizes the space available to engage the insert 14, and more closely matches the cross-section of the vagina.

The withdrawal member 32 can be constructed from various types of strings, threads or ribbons. A thread or ribbon made from 100 percent cotton fibers works well. The withdrawal member 32 can be dyed and/or treated with an anti-wicking agent, such as wax, before being secured to its respective insert 14. The anti-wicking agent will reduce body fluids from wicking along the withdrawal member 32. In other embodiments, the withdrawal member 32 may be formed from a thermoplastic, such as polypropylene or nylon.

The incontinence insert 14 is preferably made of a generally non-absorbent and soft material. An "incontinence insert" as used herein refers to devices specifically designed, configured, and/or adapted for placement into a vagina in order to reduce the occurrence and/or severity of female urinary incontinence. Typically, the insert 14 is positioned in the upper one-third of the vaginal channel. While incontinence inserts are typically made of non-absorbent materials, at least partially absorbent materials may also be used. However, because there is no intent to absorb any bodily fluids, and because the incontinence inserts are adapted and configured to provide structural support to the musculature and body tissue located near the urethro-vaginal myofascial area, incontinence inserts are readily distinguishable from catamenial tampons.

The insert 14 is designed to expand from a contracted position into an expanded position. The expansion may be accomplished by making the entire insert 14 from an expandable resilient material, or the insert 14 may include one or more layers of resilient material, or may be combined with other layers of non-resilient or relatively less resilient materials. The expansion of the insert 14 provides a stable backdrop to the musculature and body tissue located near the urethro-vaginal myofascial area and creates an environment where the urethra can be compressed upon itself during episodes of increased intra-abdominal pressure. In addition, the expansion of the insert 14 in the vagina will assist the urinary sphincter muscle in maintaining a circular cross-sectional configuration. When this circular crosssectional configuration is maintained, the sphincter muscle is able to close properly and decrease the tendency for the involuntary escape of urine.

The devices of the present invention are constructed and arranged such that the insert engages the leading end portion of the applicator when the insert is in its contracted position. In the embodiment shown in FIGS. 1A and 1B, the insert 14 includes a leading portion 36 and first and second trailing end portions 38, 40, respectively. The leading end portion 18 of the applicator 12 is adapted to engage the insert 14 in its contracted position in the cavity 28 which houses and holds the end portions 38, 40 of the insert 14 against the insert's tendency for outward expansion.

The withdrawal member 32 has a first end portion 42 adapted for attachment to the insert 14 and an opposite, trailing end portion 44. The end portion 42 of the withdrawal member is attached to one or both of the end portions 38, 40 of the insert 14, and the other end portion 44 of the withdrawal member 32 is releasibly secured to the applicator 12. The withdrawal member 32 is kept at least slightly tensioned such that end portions 38, 40 of the insert 14 do not disengage from the cavity 28 of the leading end portion 18 of the applicator 12 during insertion of the device 10.

The trailing end portion 20 has been adapted to releasably secure the withdrawal member 32. The trailing end portion 20 has a channel or aperture 46 extending from a trailing edge 22 of the applicator 12 and into the surface of a conical shape 26 which defines the surface of the trailing end portion 20 of the applicator 12. The channel or aperture 46 is sized to accommodate the withdrawal member 32, but is adapted to prevent movement of the withdrawal member in one or more directions, such as towards the leading end portion 18 of the applicator 12.

The orientation indicators 34 may be used to facilitate insertion of the device 10, and then to properly orientate the insert 14 inside the vagina so as to maximize its effectiveness. The opening to the vagina is long and narrow. The narrowest part of the leading end portion 36 of the insert 14, and the narrowest part of the elliptical shaped leading end portion 18 of the applicator 12, should be matched with the narrow dimension of the vagina. In the embodiment shown in FIGS. 1A and 1B, such an alignment would require the device to be rotated so that orientation indicators 34 are about 90 degrees from the position in which they are shown. After insertion, the device 10 can be rotated again 90 degrees so that the insert 14, after being released from the applicator 12, would generally expand so as to press against and allow for compression of the urethra and/or support the urinary sphincter muscle. The orientation indicators 34 provide the user a way to know the orientation of the insert 14 within the vagina and to guide the user in the rotation of the device 10.

After proper orientation of the insert 14, the withdrawal member 32 is released from the applicator 12 by removing the withdrawal member 32 from the aperture 46. The applicator 12 is then removed from the vagina, while the insert 14 remains inside. In some embodiments of the device, a slight rotation or twisting of the applicator may be necessary to dislodge the insert. The release of the withdrawal member 32, and thus the release of the tension on the end portions 38, 40 of the insert 14, allows the insert 14 to disengage from the leading end portion 18 of the applicator 12. The withdrawal member 32 slides through the passageway 30 as the applicator 12 is removed from the body, and the insert 14 opens to its expanded position within the body.

Figure 2A:
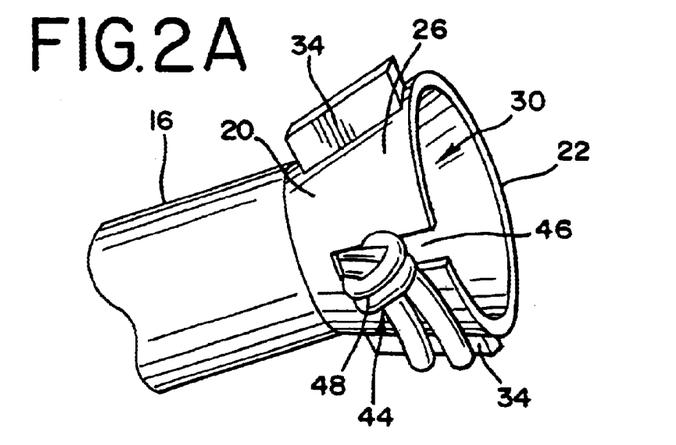
FIGS. 2A–2C are perspective views of alternate embodiments of the device of FIGS. 1A–1B.
Figure 2B:
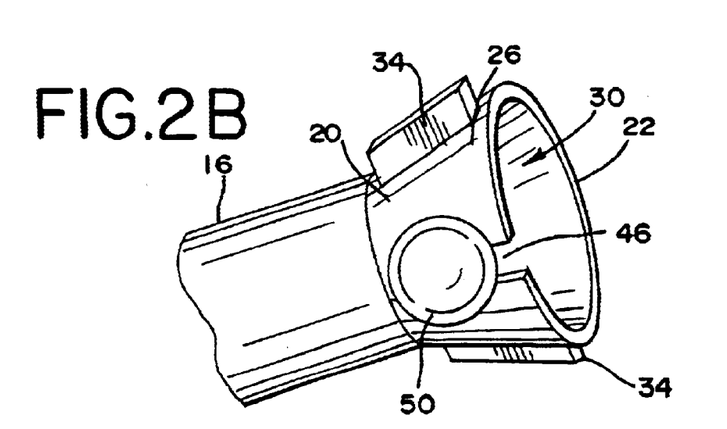
Figure 2C:
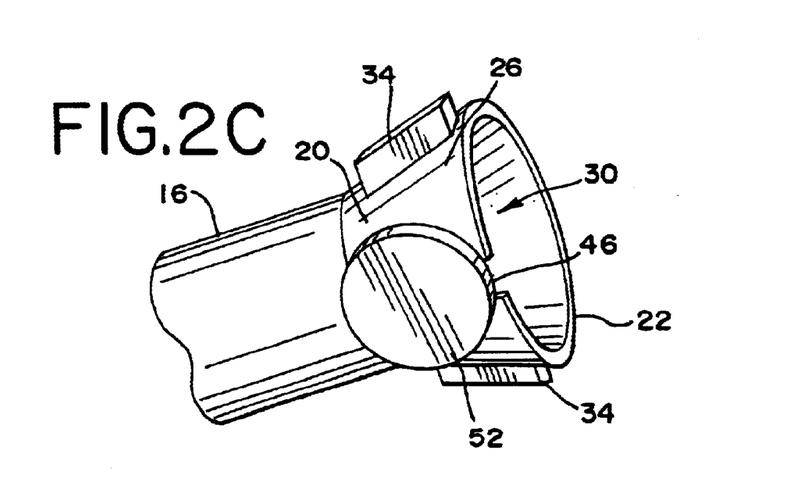

FIGS. 2A–2C illustrate particularly preferred embodiments of the trailing end portion 20 of the applicator 12 and the end portion 44 of the withdrawal member 32. In the embodiments shown, the aperture 46 is sized to prevent movement of a stopping member at the trailing end portion 44 of the withdrawal member 32, in at least the direction towards the leading end portion of the applicator 12. After the insertion of the incontinence device 10 into the body, the user manually pulls the stopping member and the trailing end portion 44 of the withdrawal member 32 out of the aperture 46 so that it can move freely through passageway 30, thus allowing separation of the insert and the single piece applicator 12, and removal of the applicator 12 from the body, while leaving the insert 14 within the body.

In FIG. 2A, the stopping member is a knot 48. The knot 48 also serves to prevent fraying of the withdrawal member 32 and to provide a place or point where a woman can grasp the withdrawal member 32 when she is ready to remove the insert 14 from her vagina.

FIG. 2B illustrates an alternate embodiment of a stopping member. The stopping member is formed as a bead 50, preferably made by melting the end of the withdrawal member 32. In this embodiment, the withdrawal member 32 is preferably made from a thermoplastic material, such as polypropylene or nylon, that will readily form a bead upon melting. FIG. 2C illustrates another embodiment of a stopping member which is a separate element, such as a disk 52, attached to the end of the withdrawal member 32.

Figures 3, 4:
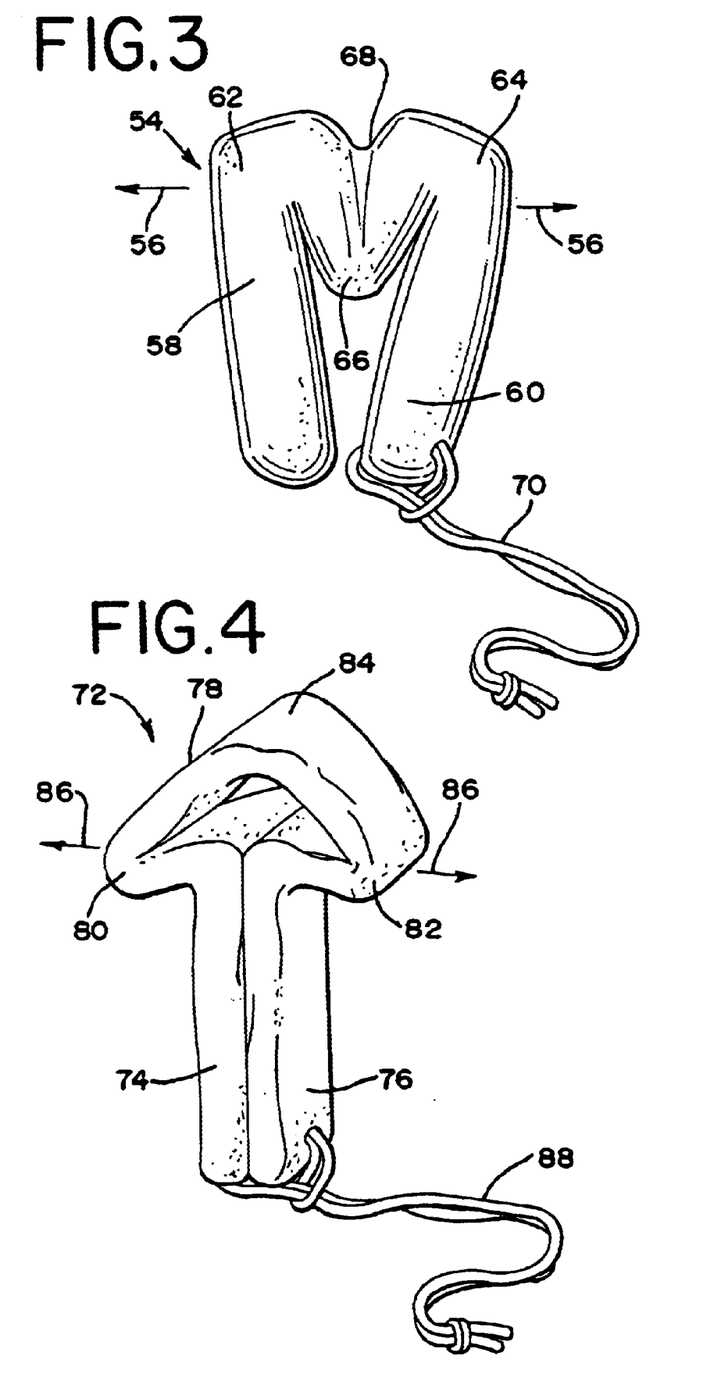
FIG. 3 is a side view of one embodiment of an insert used with the device of the present invention.
FIG. 4 is a perspective view of another embodiment of an insert used with the device of the present invention.
Figure 5A:
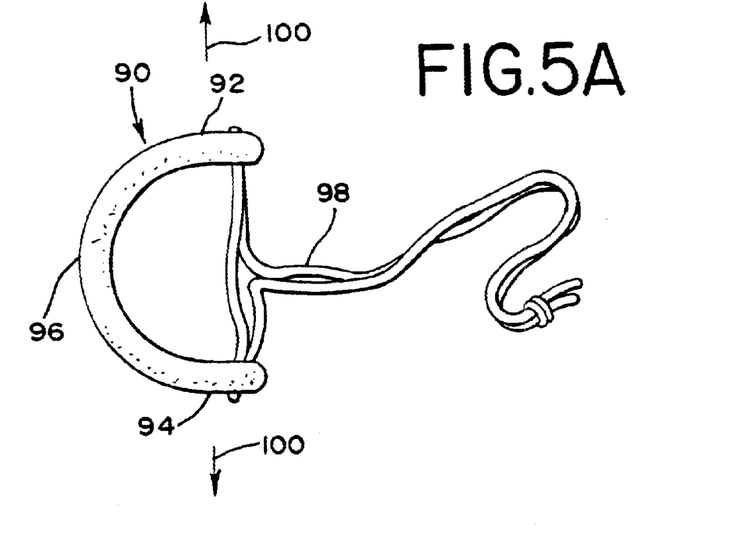
FIG. 5A is a side view of an alternate embodiment of an insert used with the device of the present invention.
Figure 5B:
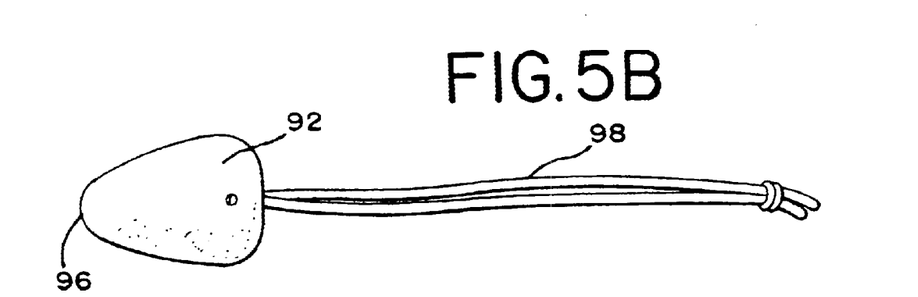
FIG. 5B is a top view of the insert of FIG. 5A.
Figure 5C:
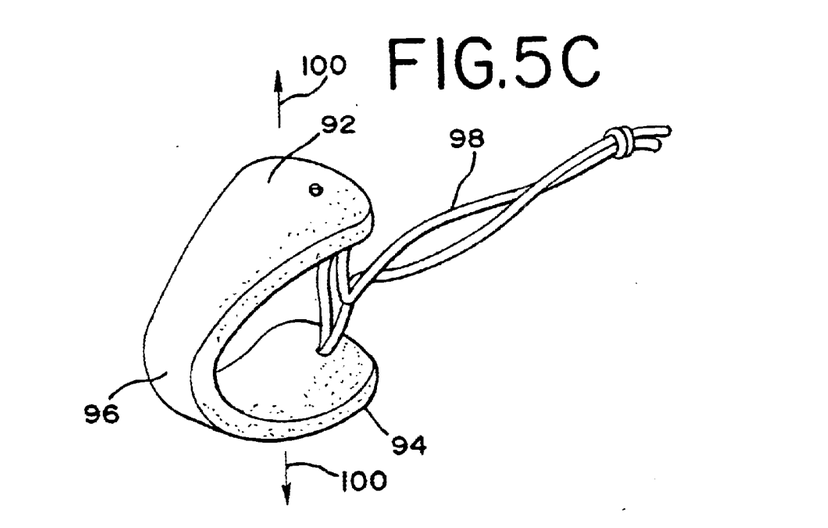
FIG. 5C is a perspective view of the insert of FIGS. 5A–5B.

FIGS. 3–5 illustrate various expandable incontinence inserts that may be used in accordance with the present invention. FIG. 3 illustrates an insert 54 having a "M-shape" profile in a plane parallel to the directions indicated by arrows 56. Such inserts are more fully disclosed in commonly assigned U.S. Pat. No. 6,142,928, entitled "Urinary Incontinence Device and a Method of Making the Same;" U.S. application Ser. No. 09/675,459, entitled "A Urinary Incontinence Device and a Method of Making Same," filed Sep. 28, 2000; and in U.S. application Ser. No. 09/675,460, entitled "Resilient Incontinence Insert and a Method of Making the Same," filed Sep. 28, 2000, all of which are hereby incorporated by reference in their entireties. Briefly, the insert 54 is formed from an elongated member having a first end portion 58 and a second end portion 60, and has three folds, 62, 64, and 66. The first end portion 58 and the second end portion 60 are aligned generally adjacent to each other and, together with the folds 62, 64, 66, form a generally planar M-shaped profile. An inward crease 68 is formed between the fold 62 and the fold 64, and opposite the fold 66. One or both of the end portions are attached to a withdrawal member, such as a string 70. The insert 54 preferably includes, or is predominately made from, a resilient material that functions to expand the insert 54 in at least a direction indicated by arrows 56 once the insert 54 is placed within the vagina.

In order for the insert 54 to be most effective in reducing the occurrence and/or severity of incontinence, the insert 54 should be properly placed and correctly oriented within the vagina. Specifically, the insert 54 should expand in the direction 56 so as to press against and allow for compression of the urethra and/or support the urinary sphincter muscle, thereby reducing the occurrence and/or severity of incontinence, as more fully described in U.S. Pat. No. 6,142,928.

FIG. 4 illustrates an alternate embodiment of an incontinence insert 72 which has a generally "dome-shaped" profile. Such inserts are more fully disclosed in U.S. Pat. Nos. 6,090,038 and 6,090,098, and in commonly assigned, co-pending U.S. application Ser. No. 09/675,460, entitled "Resilient Incontinence Insert and a Method of Making the Same," filed Sep. 28, 2000, all of which are incorporated herein by reference in their entireties. Briefly, the insert 72 is formed from an elongated member that includes a first end portion 74 and a second end portion 76, and a connecting portion 78. The first end portion 74 and the second end portion 76 are aligned adjacent to each other, and the connecting portion 78 includes three folds 80, 82, 84 in order to form a generally planar closed-loop, dome-shaped profile. The dome-shaped profile is in a plane parallel to the direction indicated by arrows 86. In this embodiment, both end portions 74, 76 are attached to a withdrawal member 88. The insert 72 preferably includes, or is predominately made from, a resilient material that functions to expand the insert 72 in at least a direction indicated by arrows 86 once the insert 72 is placed within the vagina. Like the insert of FIG. 3, the insert 72 should be properly placed and oriented within the vagina to maximize its effectiveness. The insert 72 must expand in the direction 86 so as to press against and allow for compression of the urethra and/or allow for support of the urinary sphincter muscle, thereby reducing the occurrence and/or severity of incontinence, as more fully described in U.S. Pat. Nos. 6,090,038 and 6,090,098.

FIGS. 5A–5C illustrate another embodiment of an incontinence insert in accordance with the present invention. The insert 90 includes a first end portion 92, a second end portion 94, and a connecting portion 96. A withdrawal member 98 is preferably attached at one or both of the first and second end portions 92, 94. The portions 92, 94, and 96 are integrally joined and form a generally C-shaped profile (in a plane parallel to the paper in FIG. 5A) when the insert 90 is in its expanded position. As shown in FIGS. 5B and 5C, the insert 90 is tapered such that the first and second end portions 92, 94 are wider than the connecting portion 96 in a direction generally normal to a plane defined by the C-shaped profile. Like the inserts of FIGS. 3 and 4, the insert 90 preferably includes, or is predominately made from, a resilient material that functions to expand the insert 90 in at least a direction indicated by arrows 100 once the insert 90 is placed within the vagina.

As stated above, the inserts preferably include a resilient material, either as a layer or portion of the insert, or as the predominant or sole material of the insert. Resilient materials from which portions of the inserts can be formed include natural materials such as rubber and wool; synthetic materials such as polyolefins, polyurethanes, polyethylene oxide (PEO), polyvinyl alcohol (PVA), as well as blends thereof; and fibrous materials such as polyolefin based fibers, polyethylene oxide fibers, hydrophobic rayon fibers and the like, which preferably will have characteristics similar to those of a resilient foam. The resilient portion of the inserts can also be formed from twisted, curled or cross-linked cellulose fibers or a mixture thereof, or from an open cell or a closed cell foam.

Useful non-absorbent materials for combination with the resilent materials include nylons, rayons, spun cellulose, LYCRA®, KEVLAR®, carbon fibers and the like. "LYCRA" and "KEVLAR" are trademarks of E. I. DuPont de Nemours & Company having an office at 1007 Market Street, Wilmington, Del. One such non-absorbent is a web made from bicomponent fibers which are commercially available from Chisso Corporation having an office at 1411 Broadway, 35th floor, New York, N.Y. Such fibers are sold under the name "Chisso ESC Bicomponent Fiber" and consist of a polypropylene core surrounded by a polyethylene sheath. A typical fiber that works well will have a denier, for example, of about 3, and a length, for example, of about 35–40 millimeters. Other bicomponent fibers made from polypropylene, polyethylene, etc. are commercially available from suppliers such as Exxon Mobil Corporation, having an office at 5959 Las Colinas Boulevard, Irving, Tex. 75039, and Dow Chemical, having an office at 2030 Dow Center, Midland, Mich. 48674, as well as from other vendors.

Figure 6A:
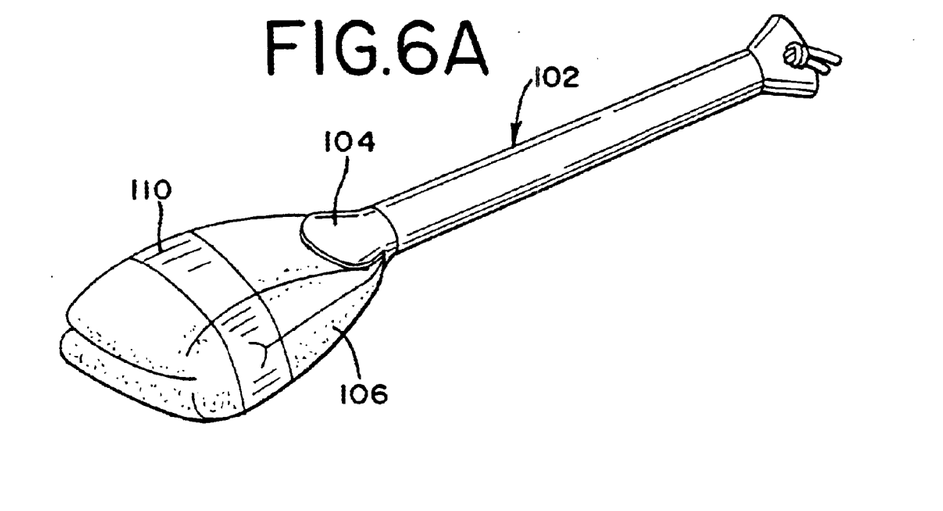
FIG. 6A is a perspective view of an alternate embodiment of a device according to the present invention.
Figure 6B:
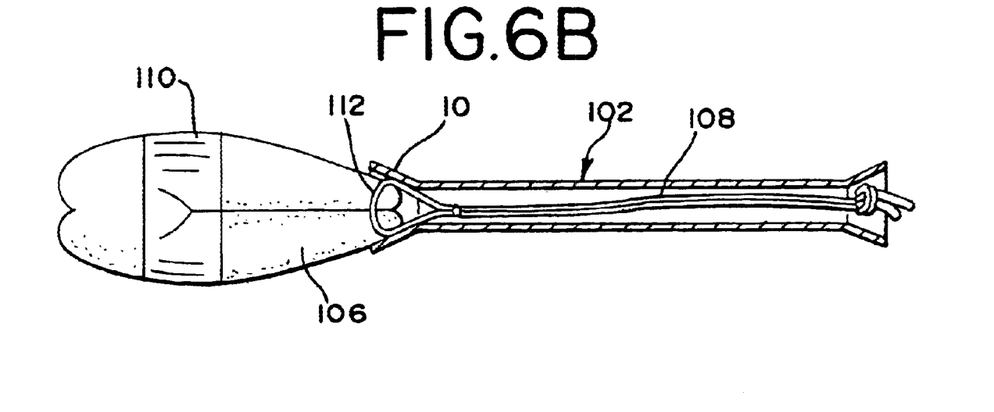
FIG. 6B is a cross-sectional view of the device of FIG. 6A.

FIGS. 6A–6B illustrate an alternate embodiment of a device according to the present invention. As shown in FIG. 6A, applicator 102 includes a leading end portion 104 that is clam-shaped, thereby further facilitating separation of the applicator 102 from the insert 106 by slight rotation of the applicator after it has been inserted and the withdrawal member 108 has been released. Furthermore, a dissolvable band 110 has been added to the surface of the insert 106. The dissolvable band 110 holds the insert 106 against expansion prior to use, but dissolves when placed in contact with moisture inside the body. In the preferred embodiment, the dissolvable band is made from a starch-based film with a pH of about 3.5 to about 6.5, which is generally of the same magnitude of the pH typically found in the vagina. Suitable materials for the dissolvable band 110 include lypholized mucin; a mucopolysacharride polymer matrix; polymers such as xanthan gum or hydroxypropyl cellulose, which are stabilized with antimicrobials and antibioadhesion chemicals such as zosteric acid; and anhydrous systems such as a neutral triglyceride wax. One example of a suitable material is Softisan 378, sold by Sasol North America, Inc. (formerly the Condea Vista Company), having an office at 900 Threadneedle, Suite 100, Houston, Tex. 77079.

In the embodiment shown, the dissolvable band 110 is used in addition to a cavity 112 and a withdrawal member 108 for holding the insert 106; however, in alternate embodiments, the dissolvable band 110 may be used in place of one or both of the cavity 112 and the withdrawal member 108. Moreover, while in the embodiment shown, the dissolvable band 110 covers only a portion of the outer surface of the insert 106, in alternate embodiments, the band 110 may cover the entire surface of the insert 106. Furthermore, in another alternate embodiment, a dissolvable coating is used around at least a portion of the insert.

Figure 7A:
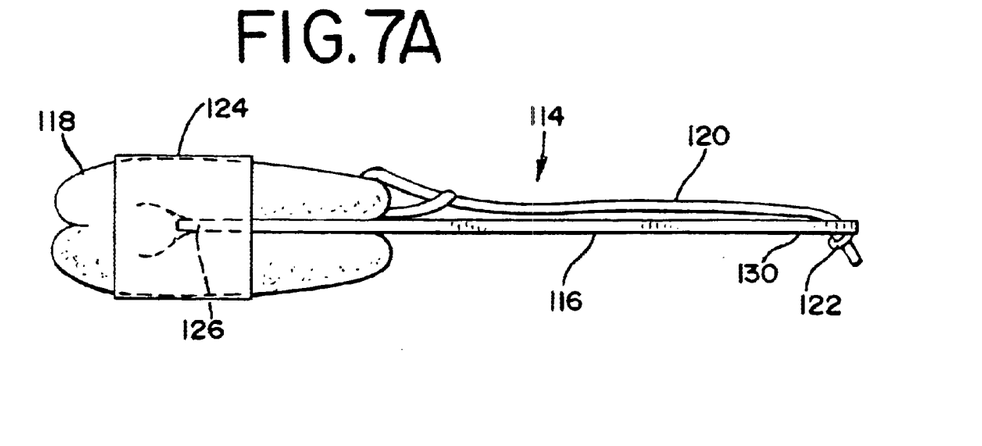
FIG. 7A is a side view of an alternate embodiment of a device according to the present invention.
Figure 7B:
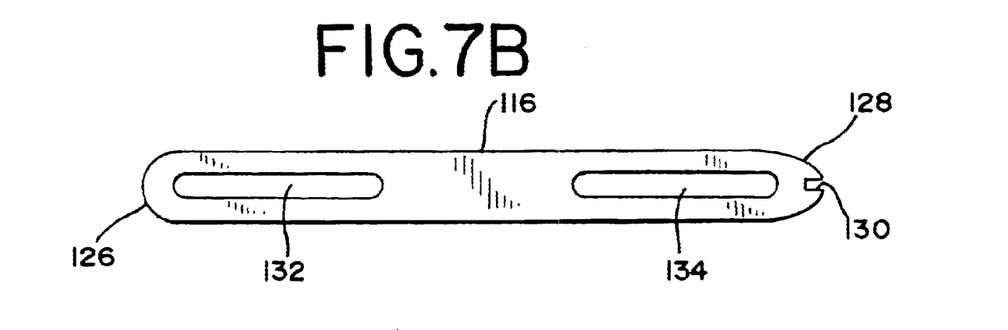
FIG. 7B is a cross-sectional view of the device of FIG. 7A.

In an alternate embodiment of the present invention, shown in FIGS. 7A and 7B, a urinary incontinence device 114 includes an elongated, generally flat and planar single piece applicator 116, an insert 118, a withdrawal member 120 having a stopping member 122, and a dissolvable band 124. Although the stopping member 122 shown in FIGS. 7A and 7B is formed as a knot, those skilled in the art will appreciate that the stopping member could be formed as a bead, a washer, a disk, or any other suitable shape. The applicator 116 has a leading end portion 126 and a trailing end portion 128 having an aperture 130. The aperture 130 accommodates the withdrawal member 120 but prevents passage of the stopping member 122 and thus prevents movement of the withdrawal member 120 in at least one direction, such as generally towards the leading end portion 126. The leading end portion 126 of the applicator 116 has no features that secure or hold the insert 118; rather, the dissolvable band 124 secures the insert 118 in its contracted position, and the withdrawal member 120, when at least slightly tensioned, cooperates to hold the insert 118 in engagement with the applicator 116. The device preferably includes cut-out portions 132, 134, which help limit the overall weight of the device, as well as provide a gripping portion for the user. After insertion, body moisture dissolves the band 124, and the user releases the stopping member 122 from the aperture 130. As the insert 118 opens to its expanded state, the insert 118 is separated from the applicator 116, which is removed from the body.

In accordance with another aspect of the present invention, a method is provided for placing an incontinence insert within a vagina. The method includes (1) inserting an incontinence device having an insert and single piece applicator into a vagina, (2) releasing the insert from the single piece applicator, and (3) removing the single piece applicator from the vagina. Depending upon the embodiment of the device used in the method, the releasing of the insert from the single piece applicator may entail either releasing the withdrawal member from the applicator, or dissolving a coating or band placed around the insert, or twisting of the applicator, or any combination of the above.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A device for reducing the occurrence of female incontinence, comprising:
   a. an expandable insert adapted to be placed in a vagina to at least partially reduce incontinence, said insert having a first end portion and a second end portion:
   b. a withdrawal member attached to at least one of said first end portion and said second end portion of said insert, said withdrawal member including a stopping member;
   c. a single piece applicator having
      i. a leading end portion having a first end engaging the incontinence insert and a second end, the leading end portion being substantially conical with a cross-section of the first end being greater than a cross-section of the second end, and
      ii. a trailing end portion adapted to releasably secure said stopping member against movement in a least one direction.

2. The device of claim 1, wherein said trailing end portion of said single piece applicator comprises a channel adapted to receive said withdrawal member.

3. The device of claim 1, wherein said single piece applicator has a hollow interior through which said withdrawal member passes.

4. The device of claim 1, wherein the leading end portion has a generally elliptical cross-section.

5. The device of claim 1, wherein said single piece applicator comprises at least one orientation indicator.

6. The device of claim 1, wherein said stopping member is selected from the group consisting of a knot, a bead, and a disk.

7. The device of claim 1 wherein said insert includes a connecting portion disposed between said first end portion and said second end portion.

8. The device of claim 7 wherein said insert, in an expanded position, defines a C-shaped profile.

9. The device of claim 7 wherein said first end portion and second end portion of said insert, in a contracted position, engage said first end of said leading end portion of said applicator.

10. A device for reducing the occurrence of female incontinence, comprising:
    a. an expandable insert adapted to be placed in a vagina to at least to at least partially reduce incontinence, said insert having an expanded position and a contracted position; and
    b. a single piece applicator having a trailing end portion and a leading end portion, with a first end engaging said insert while said insert is in its contracted position and a second end, said leading end portion being substantially conical with a cross-section of the first end being greater than a cross-section of the second end.

11. The device of claim 10, wherein said leading end portion is adapted to secure said insert in its contracted position.

12. The device of claim 10, further comprising a withdrawal member attached with said insert.

13. The device of claim 12, wherein said withdrawal member includes a stopping member.

14. The device of claim 13, wherein said trailing end portion is adapted to secure said stopping member against movement in at least one direction.

15. The device of claim 10, further comprising a dissolvable band around at least a portion of said insert, said band adapted to hold said insert in its contracted position.

16. The device of claim 10, wherein said single piece applicator comprises at least one orientation indicator.

17. The device of claim 10 wherein said insert includes a connecting portion disposed between a first end portion and a second end portion.

18. The device of claim 17 wherein said first end portion and second end portion of said insert, in a contracted position, engage said first end of said leading end portion of said applicator.

19. The device of claim 10 wherein said insert, in an expanded position, defines a C-shaped profile.

20. A method of using an incontinence insert within a vagina, comprising:
  a. inserting an incontinence device into a vagina, said device including
    (i) an expandable insert adapted to at least partially reduce incontinence, said insert having a first end portion and a second end portion;
    (ii) a withdrawal member attached to at least one of said first end portion and said second end portion of said incontinence insert, said withdrawal member including a stopping member; and
    (iii) a single piece applicator having a leading end portion and a trailing end portion, said leading end portion having a first end engaging said insert and a second end, said leading end portion being substantially conical with a cross-section of said first end being greater than a cross-section of said second end, and said trailing end portion adapted to releasably secure said stopping member against movement in at least one direction;
  b. releasing said insert from said single piece applicator; and
  c. withdrawing said single piece from the vagina.

21. The method of claim 20, wherein said device further comprises a withdrawal member having a first and second end portion, said first end portion attached with said insert and second end portion releasably secured against movement in at least one direction by said applicator; and wherein releasing said insert includes releasing said withdrawal member from said applicator.

22. The method of claim 20, wherein said device further comprises a dissolvable band positioned around at least a portion of said insert to releasably hold said insert against expansion; and wherein releasing said insert includes dissolving said band.

* * * * *